(12) United States Patent
Hayes et al.

(10) Patent No.: US 7,687,082 B2
(45) Date of Patent: Mar. 30, 2010

(54) COMPLEMENTARY COMPOSITIONS TO REDUCE BLOOD GLUCOSE LEVELS AND TREAT DIABETES

(75) Inventors: Eric S. Hayes, Seattle, WA (US); Alexander B. Zolotoy, Richmond (CA)

(73) Assignee: Astrum Therapeutics Pty. Ltd., Melbourne (AU)

( * ) Notice: Subject to any disclaimer, the term of this patent is extended or adjusted under 35 U.S.C. 154(b) by 0 days.

(21) Appl. No.: 11/400,777

(22) Filed: Apr. 7, 2006

(65) Prior Publication Data
US 2006/0251736 A1    Nov. 9, 2006

Related U.S. Application Data

(60) Provisional application No. 60/669,682, filed on Apr. 7, 2005.

(51) Int. Cl.
A61K 36/00    (2006.01)
A61K 33/06    (2006.01)
(52) U.S. Cl. .................................. 424/725; 424/682
(58) Field of Classification Search ................. None
See application file for complete search history.

(56) References Cited

U.S. PATENT DOCUMENTS

| | | | |
|---|---|---|---|
| 5,773,004 A * | 6/1998 | Takahashi | |
| 5,962,030 A | 10/1999 | Fine | |
| 6,207,714 B1 * | 3/2001 | Clouatre et al. | |
| 6,376,549 B1 * | 4/2002 | Fine et al. | |
| 6,562,836 B1 | 5/2003 | Szarek et al. | |
| 6,787,163 B2 | 9/2004 | Harris et al. | |
| 2002/0098247 A1 * | 7/2002 | Komorowski et al. | |
| 2002/0147153 A1 * | 10/2002 | Bell et al. | 514/21 |
| 2003/0203973 A1 | 10/2003 | Cooper et al. | |
| 2004/0028751 A1 * | 2/2004 | Mae et al. | |
| 2005/0020535 A1 * | 1/2005 | Vuksan | |
| 2005/0119218 A1 * | 6/2005 | Prasad et al. | 514/52 |

FOREIGN PATENT DOCUMENTS

| CA | 2 310 513 A1 | 11/2001 |
|---|---|---|
| WO | WO 00/57721 A2 | 10/2000 |

OTHER PUBLICATIONS

Simpson et al., The prevention of type 2 diabetes-lifestyle change or pharmacotherapy? A challenge for the 21st century. Diabetes Research and Clinical Practice 59 (2003) 165-180.*
Anderson, R.A. et al., "Chromium, Glucose Intolerance and Diabetes," *Journal of the American College or Nutrition* 17(6): 548-555, 1998.
Basic Summary for Type 2 diabetes. Available from www.wrongdiagnosis.com/d/diab2/basics.htm. Downloaded Jun. 28, 2006.
Bierhaus, A. et al., "Advanced glycation end product-induced activation of NF-kappa-B is suppressed by alpha-lipoic acid in cultured endothelial cells," *Diabetes* 46(9): 1481-1490, Sep. 1997.
Blumenthal, S.A., "Inhibition of gluconeogenesis in rat liver by lipoic acid. Evidence for more than one site of action," *Biochem. Journal* 219: 773-780, 1984.
Borcea, V. et al., "α-Lipoic Acid Decreases Oxidative Stress Even in Diabetic Patients with Poor Glycemic Control and Albuminuria," *Free Radical Biology & Medicine* 22(11/12): 1495-1500, 1999.
Bunin, A.Y. et al., "Glutathione Deficiency in Open-Angle Glaucoma and Approaches to Its Correction," *Vestn. Oftalmol.* 108: 13-15, 1992.
Burke, J.P. et al., "Rapid Rise in the Incidence of Type 2 Diabetes From 1987 to 1996. Results From the San Antonio Heart Study," *Archives of Internal Medicine* 159: 1450- 1456, Jul. 12, 1999.
Chang, F.-Y. et al., "Decreased cell-mediated immunity in patients with non-insulin-dependent diabetes mellitus," *Diabetes Research and Clinical Practice* 28: 137-146, 1995.
Chen, H.-L. et al., "Konjac Supplement Alleviated Hypercholesterolemia and Hyperglycemia in Type 2 Diabetic Subjects—A Randomized Double-Blind Trial," *Journal of the American College of Nutrition* 22(1): 36-42, 2003.
Cheng-Yu, H. et al., "Effect of Konjac Food on Blood Glucose Levels in Patients with Diabetes," *Biomedical and Environmental Sciences* 3: 123-131, 1990.
Cohen, M.P. et al., "Glycated albumin increases oxidative stress, activates NF-κB and extracellular signal-regulated kinase (ERK), and stimulates ERK-dependent transforming growth factor-$\beta_1$ production in macrophage RAW cells," *J. Lab. Clin. Med.* 141:242-249, 2003.
Cooper, G.J.S. et al., "Regeneration of the Heart in Diabetes by Selective Copper Chelation," *Diabetes* 53: 2501-2508, Sep. 2004.
Corica, F. et al., "Effects of oral magnesium supplementation on plasma lipid concentrations in patients with non-insulin-dependent diabetes mellitus," *Magnesium Research* 7(1): 43-47, 1994.
Corsonello, A. et al., "Serum Ionized Magnesium Levels in Type 2 Diabetic Patients with Microalbuminuria or Clinical Proteinuria," *American Journal of Nephrology* 20: 187-192, 2000.
Daimon, M. et al., "Decreased Serum Levels of Adiponectin Are a Risk Factor for the Progression to Type 2 Diabetes in the Japanese Population. The Funagata Study." *Diabetes Care* 26(7): 2015-2020, Jul. 2003.
Davis, C.M. et al., "Isolation and Characterization of a Biologically Active Chromium Oligopeptide from Bovine Liver," *Archives of Biochemistry and Biophysics* 339(2): 335-343, Mar. 15, 1997.
Delva, P. et al., "Intralymphocyte Free Magnesium and Plasma Triglycerides," *Life Sciences* 62(24): 2231-2240, 1998.

(Continued)

*Primary Examiner*—Michele Flood
*Assistant Examiner*—Qiuwen Mi
(74) *Attorney, Agent, or Firm*—Seed IP Law Group PLLC

(57) ABSTRACT

Serial administration of two complementary compositions effectively reduces and stabilizes glucose levels in the blood of mammals, specifically in pre-diabetic patients and patients with type 2 diabetes mellitus (T2DM). The first composition (Comp1) comprises (−)-hydroxycitric acid ((−)-HCA), magnesium salt (Mg) and konjac mannan (KM). The second composition (Comp2) comprises chromium picolinate (CrPic), magnesium salt (Mg) and alpha-lipoic acid (α-LA). The second composition may include one or more of Comp1, cinnamon extract (CE) and American ginseng (AG).

16 Claims, No Drawings

OTHER PUBLICATIONS

Desfaits, A.-C. et al., "Normalization of Plasma Lipid Peroxides, Monocyte Adhesion, and Tumor Necrosis Factor-α Production in NIDDM Patients After Gliclazide Treatment," *Diabetes Care* 21(4): 487-493, Apr. 1998.

Devaraj, S. et al., "Low-Density Lipoprotein Postsecretory Modification, Monocyte Function, and Circulating Adhesion Molecules in Type 2 Diabetic Patients With and Without Macrovascular Complications. The Effect of α-Tocopherol Supplementation," *Circulation* 102: 191-196, 2000.

Diabetes mellitus, Type 2. Available form www.5mcc.com/Assets/SUMMARY/TP0264.html. Downloaded Jun. 28, 2006.

Doi, K. et al., "Treatment of Diabetes with Glucomannan (Konjac Mannan)," *The Lancet* 1:987-988, May 5, 1979.

Doi K., "Effect of konjac fibre (glucomannan) on glucose and lipids," *European Journal of Clinical Nutrition* 49(suppl. 3): S190-S197, 1995.

Dunstan, D.W. et al., "The Rising Prevalence of Diabetes and Impaired Glucose Tolerance. The Australian Diabetes, obesity and Lifestyle Study," *Diabetes Care* 25(5): 829-834, May 2002.

Ekin, S. et al., "Serum Sialic Acid Levels and Selected Mineral Status in Patients with Type 2 Diabetes Mellitus," *Biological Trace Element Research* 94: 193-201, 2003.

Esposito, K. et al., "Inflammatory Cytokine Concentrations Are Acutely Increased by Hyperglycemia in Humans. Role of Oxidative Stress," *Circulation* 106: 2067-2072, 2002.

Esposito, K. et al., "Meal modulation of circulating interleukin 18 and adiponectin concentrations in healthy subjects and in patients with type 2 diabetes mellitus," *Am. J. Clin. Nutr.* 78: 1135-1140, 2003.

Fernández-Real, J.M. et al., "Novel Interaction of Adiponectin with the Endocrine System and Inflammatory Parameters," *The Journal of Clinical Endocrinology & Metabolism* 88(6): 2714-2718, 2003.

Forcasting the growth of diabetes treatments, Jun. 11, 2002. Available from www.ims-global.com/insight/new_story/0206/news_story_020611.htm. Downloaded Jun. 28, 2006.

Fuchs, J. et al., "Studies on Lipoate Effects on Blood Redox State in Human Immunodeficiency Virus Infected Patients," *Arzneim.-Forsch./Drug Res.* 43: 1359-1362, 1993.

Gadon, M.E. et al., "New-Onset Asthma after Exposure to the Steam System Additive 2-Diethylaminoethanol. A Descriptive Study." *Journal of Occupational Medicine* 36(6): 623-626, Jun. 1994.

Ghosh, D. et al., "Role of chromium supplementation in Indians with type 2 diabetes mellitus," *Journal of Nutritional Biochemistry* 13: 690-697, 2002.

Han, D. et al., "Lipoic acid increases de novo synthesis of cellular glutathione by improving cystine utilization," *BioFactors* 6: 321-338, 1997.

Henriksson, F., "Application of Economic Models in Healthcare. The Introduction of Pioglitazone in Sweden," *Pharmacoeconomics* 20(suppl. 1): 43-53, 2002.

Hinz, J.P. et al., "Evaluation of the Inhalation Toxicity of Diethylethanolamine (DEEA) in Rats," *Fundamental and Applied Toxicology* 18: 418-424, 1992.

Hofmann, M.A. et al., "Insufficient Glycemic Control Increases Nuclear FactorκB Binding Activity in Peripheral Blood Mononuclear Cells Isolated From Patients With Type 1 Diabetes," *Diabetes Care* 21(8): 1310-1316, Aug. 1998.

Ide, N. et al., "Garlic Compounds Minimize Intracellular Oxidative Stress and Inhibit Nuclear Factor-κB Activation," *Journal of Nutrition* 131: 1020S-1026S, 2001.

Iskra, M. et al., "Concentrations of Calcium, Magnesium, Zinc and Copper in Relation to Free Fatty Acids and Cholesterol in Serum of Atherosclerotic Men," *J. Trace Elem. Electrolytes Health Dis.* 7: 185-188, 1993.

Itoh, K. et al., "The effect of high oral magnesium supplementation on blood pressure, serum lipids and related variables in apparently healthy Japanese subjects," *British Journal of Nutrition* 78: 737-750, 1997.

Jacob, S. et al., "Oral Administration of RAC-α-Lipoic Acid Modulates Insulin Sensitivity in Patients with Type-2 Diabetes Mellitus: A Placebo-Controlled Pilot Trial," *Free Radical Biology & Medicine* 27(3/4): 309-314, 1999.

Jacob, S. et al., "The antioxidant alpha-lipoic acid enhances insulin-stimulated glucose metabolism in insulin-resistant rat skeletal muscle," *Diabetes* 45(8): 1024-1029, Aug. 1996.

Jacob, S. et al., *Arzneim.-Forsch./Drug Res.* 45(8): 872-874, 1995.

Jena, B.S. et al., "Chemistry and Biochemistry of—Hydroxycitric Acid from *Garcinia*," *J. Agric. Food Chem.* 50: 10-22, 2002.

Kern, P.A. et al., "Adiponectin Expression From Human Adipose Tissue. Relation to Obesity, Insulin Resistance, and Tumor Necrosis Factor-α Expression," *Diabetes* 52: 1779-1785, Jul. 2003.

Khamaisi, M. et al., "Lipoic Acid Acutely Induces Hypoglycemia in Fasting Nondiabetic and Diabetic Rats," *Metabolsim* 48(4): 504-510, Apr. 1999.

Kimura, M. et al., "Tissue Manganese Levels and Liver Pyruvate Carboxylase Activity in Magnesium-Deficient Rats," *Biological Trace Element Research* 52:171-179, 1996.

Konrad, T. et al., "α-Lipoic Acid Treatment Decreases Serum Lactate and Pyruvate Concentrations and Improves Glucose Effectiveness in Lean and Obese Patients With Type 2 Diabetes," *Diabetes Care* 22(2): 280-287, Feb. 1999.

Kvasnička, J. et al., "Haemostasis Cytoadhesive Molecules (E-Selectin and ICAM-1) and Inflammatory Markers in Non-Insulin Dependent Diabetes Mellitus (NIDDM)," *Sbornik lékařský* 99(2): 97-101, 1998.

Lal, J. et al., "Effecto of Oral Manesium Supplementation of the Lipid Profile and Blood Glucose of Patients with Type 2 Diabetes Mellitus," *J. Assoc. Physicians India* 51: 37-42, Jan. 2003.

Leung, H.-W. et al., "Developmental Toxicity Study in Sprague-Dawley Rats by Whole-body Exposure to N,N-Diethylethanolamine Vapor," *Journal of Applied Toxicology* 18: 191-196, 1998.

Mantovani, G. et al., "The Impact of Different Antioxidant Agents alone or in Combination on Reactive Oxygen Species, Antioxidant Enzymes and Cytokines in a Series of Advanced Cancer Patients at Different Sites: Correlation with Disease Progression," *Free Radical Research* 37(2): 213-223, 2003.

Miyazaki, Y. et al., "Tumor necrosis factor α and insulin resistance in obese type 2 diabetic patients," *International Journal of Obesity* 27: 88-94, 2003.

Monzillo, L.U. et al., "Effect of Lifestyle Modification on Adipokine Levels in Obese Subjects with Insulin Resistance," *Obesity Research* 11(9): 1048-1054, Sep. 2003.

Morigi, M. et al., "Leukocyte-endothelial Interaction Is Augmented by High Glucose Concentrations and Hyperglycemia in a NF-κB-dependent Fashion," *Journal of Clinical investigation* 101(9): 1905-1915, May 1998.

Moriwaki, Y. et al., "Elevated Levels of Interleukin-18 and Tumor Necrosis Factor-α in Serum of Patients With Type 2 Diabetes Mellitus: Relationship With Diabetic Nephropathy," *Metabolism* 52(5): 605-608, May 2003.

Nozue, T. et al., "Correlation of serum HDL-cholesterol and LCAT levels with the fraction of ionized magnesium in children," *Magnesium Research* 12(4): 297-301, 1999.

Pardes, H. et al., "Effects of Medical Research on Health Care and the Economy," *Science* 283(5398): 36-37, Jan. 1, 1999. Downloaded from www.sciencemag.org/cgi/content/full/283/5398/36 on Jun. 28, 2006.

Pena, L.R. et al., "Treatment With Glutathione Precursor Decreases Cytokine Activity," *Journal of Parenteral and Enteral Nutrition* 23(1): 1-6, 1999.

Preuss, H.G. et al., "Effects of a natural extract of (−)-hydroxycitric acid (HCA-SX) and a combination of HCA-SX plus niacin-bound chromium and *Gymnema sylvestre* extract on weight loss," *Diabetes, Obesity and Metabolism* 6: 171-180, 2004.

Qin, B. et al., "Cinnamon Extract Prevents the Insulin Resistance Induced by a High-fructose Diet," *Horm. Metab. Rs.* 36: 119-125, 2004.

Rabinovitz, H. et al., "Effect of Chromium Supplementation on Blood Glucose and Lipid Levels in Type 2 Diabetes Mellitus Elderly Patients," *Int. J. Vitam. Nutr. Res.* 74(3): 178-182, 2004.

Rask-Madsen, C. et al., "Tumor Necrosis Factor-α Inhibits Insulin's Stimulating Effect on Glucose Uptake and Endothelium-Dependent Vasodilation in Humans," *Circulation 108*: 1815-1821, 2003.

Rett, K. et al., "Insulin-induced glucose transporter," *Diabetes 45*(1): S66-S69, Jan. 1996.

Rivedal, E. et al., "Vanadium compounds promote the induction of morphological transformation of hamster embryo cells with no effect on gap junctional cell communication," *Cell Biology and Toxicology 6*(3): 303-314, 1990.

Roy, S. et al., "Modulation of Cellular Reducing Equivalent Homeostasis by α-Lipoic Acid," *Biochemical Pharmacology 53*: 393-399, 1997.

Spranger, J. et al, "Inflammatory Cytokines and the Risk to Develop Type 2 Diabetes. Results of the Prospective Population-Based European Prospective Investigation into Cancer and Nutrition (EPIC)-Postdam Study," *Diabetes 52*: 812-817, Mar. 2003.

Srinivasan, S. et al., "Glucose Regulates Monocyte Adhesion Through Endothelial Production of Interleukin-8," *Circulation Research 92*: 371-377, 2003.

Srivastava, V.K. et al., "The Significance of Serum Magnesium in Diabetes Mellitus," *Indian Journal of Medical Sciences 47*(5): 119-123, May 1993.

Sun, Y. et al., "The binding of trivalent chromium to low-molecular-weight chromium-binding substance (LMWCr) and the transfer of chromium from transferrin and chromium picolinate to LMWCr," *Journal of Biological and Inorganic Chemistry 5*: 129-136, 2000.

Suzuki, Y.J. et al., "α-Lipoic acid is a potent inhibitor of NF-κB activation in human T cells," *Biochemical and Biophysical Research Communications 189*(3): 1709-1715, Dec. 30, 1992.

Vincent, J.B. et al., "Elucidating a Biological Role for Chromium at a Molecular Level," *Accounts of Chemical Research 33*(7): 503-510, 2000.

Vuksan, V. et al., "Konjac-Mannan and American Ginsing: Emerging Alternative Therapies for Type 2 Diabetes Mellitus," *Journal of the American College of Nutrition 20*(5): 370S-380S, 2001.

Walsh, D.E. et al., "Effect of Glucomannan on Obese Patients: A Clinical Study," *International Journal of Obesity 8*: 289-293, 1984.

Williams, R. et al., "Assessing the impact of complications on the costs of Type II diabetes," *Diabetologia 45*: S13-S17, 2002.

Yang, W.-S. et al., "Weight Reduction Increases Plasma Levels of an Adipose-Derived Anti-Inflammatory Protein, Adiponectin," *The Journal of Clinical Endocrinology & Metabolism 86*(8): 3815-3819, 2001.

Yorek, M.A. et al., "Effect of Increased Concetration or D-Glucose of L-Fucose on Monocyte Adhesion to Endothelial Cell Monlayers and Activation of Nuclear Factor-κB," *Metabolsim 51*(2): 225-234, Feb. 2002.

Zempleni, J. et al., "Identification of biotin sulfone, bisnorbiotin methyl ketone, and tetranorbiotin-*l*-sulfoxide in human urine," *American Journal of Clinical Nutrition 65*: 508-511, 1997.

Zhang, W.-J. et al., "α-Lipoic acid inhibits TNF-α-induced NF-κB activation and adhesion molecule expression in human aortic endothelial cells," *FASEB Journal 15*: 2423-2432, 2001.

Zidek, W. et al., "Intrazelluläre Elektrolyte und Serumlipide in Abhängigkeit von der diätetischen Fettsäurenzufuhr," *Schweiz. Med. Wschr. 112*: 1787-1789, 1982.

Zimmet, P., "Diabetes Mellitus—One of Australia's top six health priorities," Nov. 2002. Available from www.healthinsite.gov.au/content/internal/. Downloaded Jun. 28, 2006.

Khan, A., et al., "Cinnamon improves glucose and lipids of people with type 2 diabetes," Diabetes Care, 26(12):3215-8, Dec. 2003.

Abraham et al., "The Effects of Chromium Supplementation on Serum Glucose and Lipids in Patients With and Without Non-Insulin-Dependent Diabetes," Metabolism, 41(7):768-771, Jul. 1992.

De Lourdes Lima et al., "The Effect of Magnesium Supplementation in Increasing Doses on the Control of Type 2 Diabetes," Diabetes Care, 21(5):682-686, May 1998.

De Valk et al., "Oral Magnesium Supplementation in Insulin-requiring Type 2 Diabetic Patients," Diabetic Medicine, 15:503-507, 1998.

Eibl et al., "Hypomagnesemia in Type II Diabetes: Effect of a 3-Month Replacement Therapy," Diabetes Care, 18 (2):188-192, Feb. 1995.

Eriksson et al., "Magnesium and Ascorbic Acid Supplementation in Diabetes mellitus," Ann. Nutr. Metab., 39:217-223, 1995.

Evans et al., "Pharmacokinetics, Tolerability and Fructosamine-Lowering Effect of a Novel, Controlled-Release Formulation of α-Lipoic Acid," Endocrine Practice, 8(1):29-35, Jan./Feb. 2002.

Gullestad et al., "Effect of Magnesium Treatment on Glycemic Control and Metabolic Parameters in NIDDM Patients," Diabetes Care, 17(5):460-461, May 1998.

Gunton et al., "Chromium Supplementation Does Not Improve Glucose Tolerance, Insulin Sensitivity, or Lipid Profile," Diabetes Care, 28(3):712-713, Mar. 2005.

Hahm et al., "Clinical experience with thioctacid (thioctic acid) in the treatment of distal symmetric polyneuropathy in Korean diabetic patients," Journal of Diabetes and Its Complications, 18:79-85, 2004.

Jacob et al., "Enhancement of glucose disposal in patients with type 2 diabetes by alpha-lipoic acid," Arzneimittelforschung, 45(8):872-874, Aug. 1995.

Jacob et al., "Oral Administration of RAC-α-Lipoic Acid Modulates Insulin Sensitivity in Patients with Type-2 Diabetes Mellitus: A Placebo-Controlled Pilot Trial," Free Radical Biology & Medicine, 27(3/4):309-314, 1999.

Konrad et al., "α-Lipoic Acid Treatment Decreases Serum Lactate and Pyruvate Concentrations and Improves Glucose Effectiveness in Lean and Obese Patients With Type 2 Diabetes," Diabetes Care, 22(2):280-287, Feb. 1999.

Lal et al., "Effect of Oral Magnesium Supplementation on the Lipid Profile and Blood Glucose of Patients with Type 2 Diabetes Mellitus," J. Assoc. Physicians India, 51:37-42, Jan. 2003.

Uusitupa et al., "Chromium supplementation in impaired glucose tolerance of elderly: effects on blood glucose, plasma insulin, C-peptide and lipid levels," British J. Nutrition, 68:209-216, 1992.

Vasques et al., "Evaluation of the Pharmacotherapeutic Efficacy of *Garcinia cambogia* plus *Amorphophallus konjac* for the Treatment of Obesity," Phytother. Res., 22:1135-1140, 2008.

Jacob et al., "Improvement of Insulin-stimulated Glucose-disposal in type 2 Diabetes after Repeated Parenteral Administration of Thioctic Acid," Exp. Clin Endocrinol. Diabetes, 104(3)284-288, 1996.

Johnsen et al., "Magnesium Implementation of Patients with Type II Diabetes," Ugeskr Laeger, 161(7):945-948, Feb. 15, 1999.

Lee et al., "Beneficial Effect of Chromium Supplementation on Serum Triglyceride Levels in NIDDM," Diabetes Care, 17(12):1449-1452, 1994.

Negrisanu et al., "Effects of 3-month Treatment with the Antioxidant Alpha-Lipoic Acid in Diabetic Peripheral Neuropathy," Rom. J. Int. Med., 37(3):297-306, 1999.

Purvis et al., "Effect of Oral Magnesium Supplementation on Selected Cardiovascular Risk factors in Non-insulin-dependent Diabetics," 3:503-507, 1998.

Rahbar et al., "Effect of L-carnitine on Plasma Glycemic and Lipidemic Profile in Patients with Type II Diabetes Mellitus," Eur. J. Clin. Nut., 59:592-596, 2005.

Reljanovic et al., "Treatment of Diabetic Polyneuropathy with the Antioxidant Thioctic Acid (α-Lipoic Acid): A Two Year Multicenter Randomized Double-blind Placebo-controlled Trial (ALADIN II)," Free. Rad. Res., 31:171-179, 1999.

Schwartz et al., "Effect of Hydroxycitrate on Hepatic de novo Lipogenesis, Gluconeogenesis and Glucose Production in Obese Hyperinsulinemic Subjects," Circulation—Supplement 1, 100(18):I-196, 1999.

Yonei, Y. et al., "Effects on the Human Body of a Dietary Supplement Containing L-carnitine and *Garcinia cambogia* Extract: A Study Using Double-blind Tests," J. Clin. Biochem. Nutr., 42:89-103, Mar. 2008.

Ziegler et al., "Treatment of Symptomatic Diabetic Peripheral Neuropathy with the Anti-oxidant α-lipoic Acid," Diabetologia 38:1425-1433, 1995.

\* cited by examiner

COMPLEMENTARY COMPOSITIONS TO REDUCE BLOOD GLUCOSE LEVELS AND TREAT DIABETES

CROSS-REFERENCE TO RELATED APPLICATION

This application claims the benefit under 35 U.S.C. § 119(e) of U.S. Provisional Patent Application No. 60/669,682 filed Apr. 7, 2005, where this provisional application is incorporated herein by reference in its entirety.

BACKGROUND OF THE INVENTION

1. Field of the Invention

The present invention relates to the prevention or treatment of type 2 diabetes mellitus (T2DM) and reduction of blood glucose levels. More specifically it relates to serial administration of two complementary compositions that effectively reduce glucose levels in the blood of mammals, including humans. The first composition (Comp1) potentiates mammalian physiological and pharmacological responses to the second composition (Comp2) which includes hypoglycemic agents.

2. Description of the Related Art

The prevalence of diabetes is increasing in developed countries and in developing countries, as they become more affluent. Sixteen million Americans have diabetes with an additional 798,000 new cases appearing annually. T2DM represents 80% of all diabetes in the USA and is increasing more rapidly in some ethnic groups (http://www.wrongdiagnosis.com/d/diab2/basics.htm; http://www.5mcc.com/Assets/SUMMARY/TP0264.html). The incidence of T2DM in non-Hispanic whites increased 300% in the decade between 1987 and 1996 (Burke J P et al. Arch Intern Med. 1999, 159:1450-1456). In Australia the prevalence of diabetes is estimated at 7.4% of the population whereas the prevalence of people exhibiting abnormal glucoses levels, and therefore at risk of developing diabetes, is 16.4%. In the latter group, there is a marked increase with increasing age: 37% of those aged 55-64 years, 47% of those aged 65-74 years, and 53% of those aged 75 years and above. The prevalence of diabetes in Australia has more than doubled since 1981 and it is expected that 1.23 million Australians will suffer from diabetes in 2010 (Dunstan D W, Diabetes Care 2002, 25:829-834; http://www.healthinsite.gov.au/content/internal/page.cfm?ObjIb=00001FB3-0318-1D2D-81CF83032BFA006D). Approximately 1 in 4 Australians aged 25 years and older has a condition of impaired glucose metabolism or clinical diabetes. The Australian and American government health regulatory agencies have stated that diabetes is one of the top health priorities (http://www.healthinsite. gov.au/content/internal/page.cfm?ObjID=00001FB3-0318-1D2D-81CF83032BFA006D). The combined population suffering from type 1 and type 2 diabetes mellitus (T1DM and T2DM) in seven major world markets is projected to grow from 39.4 million to 49.4 million from 2003 to 2010, an estimated growth rate of 25.4% (http://www.ims-global.com/insight/news_story/0206/news_story_020611.htm).

T2DM causes numerous complications such as cardiovascular disease, stroke, blindness, nerve and renal damage and inflammatory disorders. In both human and economic terms, diabetes is one of the most costly diseases in the world. The American Diabetes Association (ADA) estimates that the total direct cost associated with diabetes care each year in the USA is US$ 45 billion and growing (Pardes H, Science 1999, 283:36-37). Indirect costs are very difficult to measure, but a recent study in Sweden suggests that the indirect costs of treating diabetes are approximately 158% of the direct costs (Henriksson F, Pharmacoeconomics 2002, 20:43-53). Furthermore, complications arising from T2DM account for 3.5 fold increases in individual costs and 5.5 fold increases in hospitalization costs (Williams R et al. Diabeteologia 2002, 47:S13-S17).

One of the main contributing factors of diabetes and diabetes related diseases is hyperglycemia (persistent abnormal elevation in blood glucose levels). There is a clear unmet medical need for effective and safe medications to reduce abnormal blood glucose profiles and to treat and prevent diabetes and its ancillary pathology. In this regard, an extensive interest exists within clinical and research communities to develop natural products or compounds that are already present in mammals and act to reduce blood glucose levels.

Despite the number of compositions proposed to be useful for treating T2DM, the efficacy or safety of such compositions has typically not been reported. For example, the composition disclosed in U.S. Pat. No. 6,787,163 is proposed to regulate glucose levels and includes vanadyl sulfate, diethylethanolamine and copper. However, a possible relationship between vanadyl sulfate and cancer must be firmly considered. While literature indicates cytotoxicity of vanadyl sulfate to cancer cells, there are also reports of possible cancer causing activity of vanadyl sulfate related to DNA damage (Wozniak K, Arch Toxicol. 2004, 78:7-15). Further, vanadium compounds have been reported to promote the induction of unwanted morphological transformation of hamster embryo cells (Rivedal E et al. Cell Biol Toxicol. 1990, 6:303-314). Exposure of humans to diethylethanolamine results in symptoms of irritation, and it contributes to the development of asthma in some (0.6%) individuals (Gadon M. E. et al. J Occup Med. 1994, 36(6):623-6). Administration of 100 ppm diethylethanolamine vapor to timed-pregnant Sprague-Dawley rats for 6 hours a day results in dry rales, statistically significant reduction of body weight (by 9.5%), and reduction of weight gain (by 48%) during exposure (Leung H W et al. J Appl Toxicol. 1998, 18:191-196). Nasal cavities of rats exposed to 25 or 76 ppm of diethylethanolamine for 14 weeks revealed evidence of inflammatory cell infiltration, focal hyperplasia, and squamous metaplasia in the respiratory epithelium of the anterior nasal turbinate (Hinz J P et al. Fundam Appl Toxicol. 1992, 18(3):418-24). Copper is increased in T2DM patients and promotes heart failure. Copper chelation increases the level of copper in urine, improves copper excretion, reduces blood levels of copper, results in the alleviation of heart failure, improves cardiomyocyte structure, and is effective in the reversal of left ventricular hypertrophy and collagen and beta(1) integrin deposition (Cooper G J et al. Diabetes. 2004, 53:2501-2508; US Patent Publication 20030203973A1). Therefore, copper is expected to aggravate diabetes and its ancillary pathology.

Accordingly, there is a need in the art for methods and compositions to reduce and stabilize blood glucose levels.

BRIEF SUMMARY OF THE INVENTION

The present invention provides compositions and methods for use in the prevention or treatment of diabetes and for the reduction of blood glucose in mammals, including humans. The present invention further provides compositions and methods for use in the prevention or treatment of hyperglycemia, hyperinsulinemia, insulin resistance, oxidative stress, inflammation or side effects of diabetes associated with diabetes in mammals, including humans.

In certain embodiments, the present invention provides two compositions and is related to serial administration thereof to effectively reduce and stabilize blood glucose levels in mammals, for example in prediabetic patients and patients with type 2 diabetes mellitus. In certain other embodiments, the present invention provides two compositions and is related to serial administration thereof in the prevention or treatment of hyperglycemia, hyperinsulinemia, insulin resistance, oxidative stress, inflammation or side effects of diabetes associated with diabetes in mammals, including humans. Side effects of diabetes include, but are not limited to, neuropathy, nephropathy, cardiomyopathy, stroke and blindness.

Composition 1 (Comp1) comprises (−)-hydroxycitric acid ((−)-HCA), konjac mannan (KM), and magnesium salt. Composition 2 (Comp2) comprises chromium picolinate (CrPic), α-lipoic acid (α-LA), and magnesium salt. Comp2 may optionally include one or more of Comp1, cinnamon extract (CE) and American ginseng (AG).

In certain embodiments, the present invention provides a method for prevention or treatment of diabetes and reduction of blood glucose levels in mammals comprising administration of Comp1 and subsequent administration of Comp2. In certain other embodiments, the present invention provides a method for treatment or prevention of hyperglycemia, hyperinsulinemia, insulin resistance, oxidative stress, inflammation or side effects associated with diabetes in mammals comprising administration of Comp1 and subsequent administration of Comp2.

In certain embodiments, Comp1 may be administered for 4 to 8 weeks. In certain embodiments, Comp2 may be administered for an additional 2 to 8 weeks. In certain embodiments, compositions may be administered orally, parenterally, rectally, sublingually or via inhalation. In certain such embodiments, compositions may further include a physiologically acceptable carrier which is suitable for oral, parenteral, rectal, sublingual or inhalation administration.

Comp1 was discovered within the present invention to potentiate physiological and pharmacological responses of mammals to the specific hypoglycemic effects of Comp2. The serial administration of Comp1 and Comp2 results in an effective and safe decrease of blood glucose levels. The components of Comp1 and Comp2 are not associated with cellular, organ or systemic toxicity.

These and other aspects of the present invention will become apparent upon reference to the following detailed description. All references disclosed herein are hereby incorporated by reference in their entirety as if each was incorporated individually.

DETAILED DESCRIPTION OF THE INVENTION

The present invention discloses that, surprisingly, serial administration of two compositions effectively reduces and stabilizes blood glucose levels in mammals, which includes humans, specifically in prediabetic patients and patients with type 2 diabetes mellitus. Composition 1 (Comp1) comprises (−)-hydroxycitric acid ((−)-HCA), magnesium, and konjac mannan (KM), and is typically administered for 4-8 weeks. Composition 2 (Comp2) comprises chromium picolinate (CrPic), Magnesium, and α-lipoic acid (α-LA), and is typically administered for an additional 2-8 weeks. Comp2 may optionally include one or more of Comp1, cinnamon extract (CE) and American ginseng (AG). Comp1 was discovered within the present invention to potentiate physiological and pharmacological responses of mammals to the specific hypoglycemic effects of Comp2. The serial administration of Comp1 and Comp2 results in an effective and safe decrease of blood glucose levels. The components of Comp1 and Comp2 are not associated with cellular, organ or systemic toxicity.

Ingredients of Composition 1 (Comp1)

(−)-HCA is a potent inhibitor of adenosine triphosphate (ATP) citrate lyase, an enzyme which catalyzes the extra-mitochondrial cleavage of citrate to oxaloacetate and acetyl-CoA: citrate+ATP+CoA→acetyl-CoA+ADP+P(i)+oxaloacetate. The inhibition of this reaction limits the availability of acetyl-CoA units required for fatty acid synthesis and lipogenesis during a lipogenic diet, that is, a diet high in carbohydrates (Jena B S et al. J Agric Food Chem. 2002, 50:10-22). Administration of 2.8 g of (−)-HCA to humans resulted in decreased body weight and body mass index (BMI; −5 to −6%), decreased low density lipoprotein (LDL; −13.2%), decreased total cholesterol (TC; −7.2%), and increased high density lipoprotein (HDL; +7.3%) levels compared to baseline (Preuss H G et al. Diab Obes Metabol. 2004, 6:171-180). In addition, (−)-HCA resulted in a statistically significantly increase in the excretion of toxic compounds associated with diabetes. Accordingly, at the end of the study cited above, the urine level of the following compounds was increased compared to baseline: malondialdehyde (+88.4%), acetaldehyde (+83.1%), formaldehyde (+106.4%), and acetone (+35.6%).

Magnesium exhibits a negative correlation to total cholesterol (Srivastava V et al Ind J Med Sci. 1993, 47:119-123), triglycerides (Delva P et al. Life Sci. 1998, 62:2231-2240), free fatty acid (Iskra M et al. J Trace Elem Electrolytes Health Dis. 1993, 7:185-188) and a positive correlation to HDL cholesterol (Nozue T et al. Magnes Res. 1999, 12:297-301; Zidek V et al. Med Wochenschr. 1982, 112:1787-1789). A magnesium deficient diet results in increased phospholipid, cholesterol and triglycerides (Kimura M et al. Biol Trace Elem Res. 1996, 52:171-179), an experimental result that is in agreement with data presented above. Magnesium deficiency in diabetes has been clearly documented (Corsonello A et al. Am J Nephrol. 2000, 20:187-192; Ekin et al. Biol. Trace Element Res. 2003, 94:193-202). Magnesium supplement leads to increased levels of HDL and decreased levels of triglycerides, LDL and total cholesterol in humans (Lal J et al. J Assoc Phys Ind. 2003, 51:37-42; Itoh K et al. Br J Nutr. 1997, 78:737-50; Corica F et al. Magnes Res. 1994, 7:43-47).

Administration of konjac mannan with food results in a generalized loss of weight (by an average of 2.75 kg), decreased LDL and TC (−23% and −12.7%, respectively), and reduced fasting and postprandial levels of glucose (on average −22%) (Huang Cheng-Yu et al. Biomed Environ Sci. 1990, 3:121-131; Walsh D E et al. Int J Obes. 1984, 8:289-293; Doi K et al. Lancet. 1979, 1:987-988; Doi K, Eur J Clin Nutr. 1995, 49:S190-S197; Chen Hsaio-Ling et al. J Am Coll Nutr. 2003, 22:36-42).

Ingredients of Composition 2 (Comp2)

The mechanism of the glucose lowering effect of CrPic is associated with low molecular weight chromium binding substance (LMWCr), a protein that is present in all mammalian species. LMWCr is stored in the cytosol of insulin-sensitive cells in an apo (unbound) form that is activated by binding four chromium III ions in a multinuclear assembly much like that of calmodulin (Vincent J B, Acc Chem Res. 2000, 33:503-510). This activation is the result of a series of steps stimulated by insulin signaling. LMWCr potentiates the action of insulin once insulin has bound to its receptor (Sun Y et al. J Biol Inorg Chem. 2000, 5:129-136). This insulin potentiating or autoamplification action apparently stems from the ability of LMWCr to maintain stimulation of tyrosine kinase activity (Anderson R J, Amer Coll Nutr. 1998, 17:548-555; Vincent, 2000, supra). Once insulin is bound to its receptor, LMWCr binds to the activated receptor on the inner side of the cell membrane and increases the insulin-activated protein kinase activity by eightfold (Davis C M et al. Arch Biochem Biophys. 1997, 339: 335-343).

Studies supporting the effect of CrPic have been reported. In one such study, 39 T2DM patients having an average age of 73 years received 200 μg chromium twice daily for three weeks and were compared to 39 age-matched controls. Changes compared to baseline were as follows: reduction in glucose (−21%; $p<0.001$); glycated hemoglobin (HbA$_1$C) (from 8.2% to 7.6%; $p<0.01$); cholesterol (−9.4%; $p<0.02$); and triglycerides (−10.5%) (Rabinovitz H et al. Int J Vitam Nutr Res. 2004, 74:178-182). In another study, T2DM patients receiving 200 μg chromium as CrPic twice daily for 12 weeks exhibited improvement in fasting glucose (0.44 mM; $p<0.001$) and post-prandial serum glucose (1.97 mM; $p<0.001$), and a significant decrease in insulin level, compared to age-matched subjects receiving placebo control (Ghosh D et al. J Nutr Biochem. 2002, 13:690-697).

T2DM patients exhibit an increased level of inflammatory mediators, such as TNF-alpha, IL-6, and IL-18 (Spranger J et al. Diabetes. 2003, 52:812-817; Desfaits A C et al. Diabetes Care. 1998, 21:487-493; Chang F Y et al. Diabetes Res Clin Pract. 1995, 28:137-146; Moriwaki Y et al. Metabolism. 2003, 52:605-608; Esposito K et al. Am J Clin Nutr. 2003, 78:1135-1140). Levels of these mediators, specifically IL-18, positively correlate with the level of urinary albumin excretion in patients with microalbuminuria, a surrogate marker of diabetic nephropathy (Moriwaki Y et al, 2003, supra). Diabetic monocytes collected from T2DM patients express a greater TNF-alpha-mediated adhesion to endothelium (e.g., increase in sICAM and sE-selectin expression) compared to non-diabetic control subjects (Devaraj S et al. Circulation. 2000, 102:191-196; Kvasnicka J et al. Sb Lek. 1998, 99:97-101).

Infusion of TNF-alpha into healthy patients completely inhibits insulin-stimulated glucose uptake (Rask-Madsen C et al. Circulation. 2003, 108:1815-1821). This result was supported by the studies of Miyazaki Y et al. (Int J Obes Relat Metab Disord. 2003, 27:88-94), who found a negative correlation ($r=-0.45$, $p<0.01$) between the level of TNF-alpha and insulin-stimulated glucose disposal and a positive correlation between the level of TNF-alpha and fasting glucose and insulin levels in healthy people and patients with impaired glucose tolerance. The same studies failed to find a correlation between TNF-alpha and insulin-stimulated glucose disposal in T2DM patients. Taken together the observations described above indicate that TNF-alpha leads to an increase in plasma glucose and insulin levels prior to the onset of type 2 diabetes. There is an inverse correlation between TNF-alpha and adiponectin (protein with anti-inflammatory properties) levels in obese patients (Kern P A et al. Diabetes. 2003, 52:1779-1785; Fernandez-Real J M et al. J Clin Endocrinol Metab. 2003, 88:2714-27188). Decreased levels of adiponectin are clearly associated with type 2 diabetes (Daimon M et al. Diabetes Care. 2003; 26:2015-2020; Yang W P et al. J Clin Endocrinol Metab. 2001, 86:3815-3819; Monzillo L U et al. Obes Res. 2003, 11:1048-1054). Adiponectin correlates with insulin sensitivity ($r=0.67$, $p<0.001$) (Kern et al. 2003, supra), and analysis of 1792 residents of Japan resulted in the conclusion that low levels of adiponectin are associated with diabetes ($p=0.009$; Daimon M et al, 2003, supra).

TNF-alpha, hyperglycemia and advanced glycation end (AGE) products induce NF-kappaB activation (Suzuki Y J et al. Biochem Biophys Res Commun. 1992, 189:1709-1715; Yorek M A et al. Metabolism. 2002, 51:225-234; Bierhaus A et al. Diabetes. 1997, 46:1481-1490; Hoffman M A et al. Diabetes Care. 1998, 21:1310-1316). AGE products are associated with the elevation of adhesion markers such as E-selectin, vascular cell adhesion molecule 1 and intercellular adhesion molecule 1 and result in increased adhesion of leukocytes (monocytes) to endothelial cells (Suzuki et al. 1992, supra; Morigi M J, Clin Invest. 1998, 101:1905-1915; Srinivasan S et al. Circ Res. 2003, 92:371-377). Hyperglycemia in human (15 mmol/L for 5 hours) results in increase in the level of TNF-alpha, IL-6 and IL-18, and the effect is stronger and longer in subjects with impaired glucose tolerance compared to controls (Esposito K. et al. Circulation. 2002, 106(16): 2067-72).

Accordingly, TNF-alpha mediates many of the inflammatory cascades associated with the diabetic state.

Alpha-lipoic acid (α-LA) is an anti-oxidant that exhibits multiple effects directly against diabetes and diabetes-related diseases, including inflammation. α-LA significantly prevents NF-kappaB activation (Suzuki et al. 1992, supra; Bierhaus A et al. 1997, supra; Hoffman et al. 1998, supra; Cohen M P, J Lab Clin Med. 2003, 141:242-249), partially prevents monocyte adhesion to endothelial cells (Yorek et al. 2002, supra; Zhang W J et al. FASEB J. 2001, 15:2423-2432), reduces the level of TNF-alpha and IL-6 in cancer patients (Mantovani G et al. J Environ Pathol Toxicol Oncol. 2003; 22:17-28), decreases levels of peroxides in diabetes mellitus patients by 34% (Borcea V et al. Free Radic Biol Med. 1999, 26:1495-1500), and displays a number of anti-inflammatory properties, including increases in the level of cellular glutathione (Fuchs J et al. Arzneimittelforschung. 1993, 43:1359-1362; Bunin A et al. Vestn Oftalmol. 1992, 108:13-15; Han D et al. Biofactors. 1997; 6:321-338). By the same token, administration of glutathione to patients with alcoholic liver disease results in a significant decrease in the level of TNF-alpha, II-6 and IL-8 (Pena L R et al. J Parenter Enteral Nutr. 1999, 23:1-6). The inhibition of glutathione depletion prevents NF-kappaB activation induced by TNF-alpha (Ide N et al. J Nutr. 2001, 131:1020S-1026S).

In addition, α-LA increases the uptake of glucose into muscle (Rett K et al. Diabetes. 1996, 45:S66-S69), increases the ratio of NAD+/NADH, thus stimulating glycolysis (Roy S et al. Biochem Pharmacol. 1997, 53:393-399), and inhibits gluconeogenesis in liver of normal and diabetic rats (Khamaisi M et al. Metabolism 1999, 48:504-510). It is hypothesized that the anti-gluconeogenic effect of α-LA in liver may be attributed to a sequestration of intramitochondrial acetyl-CoA as lipoyl-CoA, bisnorlipoyl-CoA or tetranorlipoyl-CoA (Blumental S A, Biochem J. 1984, 219:773-780). A reduction in acetyl-CoA leads to decreased citrate levels and thus with the activation of phosphofructokinase to enhanced glycolysis. It has also been hypothesized that the α-LA mediated reduction of gluconeogenesis may be the result of an inhibitory effect on biotin-dependent carboxylase, an enzyme which catalyses an initial rate-limiting step in gluconeogenesis (Zemleni J, Am J Clin Nutr. 1997, 65:508).

Administration of 500 to 1800 mg of α-LA daily to patients with T2DM resulted in increases in insulin-stimulated glucose disposal (or increases in metabolic clearance of glucose) from 30% to 50% (Jacob S et al. Arzneimittelforschung 1995, 45:872-874; Jacob S et al. Diabetes 1996, 45:1024-1029; Jacob S et al. Free Radic Biol Med. 1999, 27:309-314). These results are confirmed by separate studies of lean and obese diabetes patients. Administration of 600 mg of α-LA to humans twice daily for 4 weeks resulted in increases in glucose disposal by 50% in lean T2DM subjects compared to lean controls and by 42% in obese T2DM subjects compared to obese controls (Konrad T et al. Diabetes Care 1999, 22:280-287).

Comp2 may optionally include Comp1, cinnamon extract (CE) and/or American ginseng (AG). When added to drinking water, cinnamon extract (CE; 300 mg/kg/day) improved the glucose utilization in normal male Wistar rats fed a high-fructose diet (HFD) for three weeks. HFD resulted in a 40% reduction of glucose uptake versus control, whereas CE improved glucose uptake in rats subjected to HFD diet to control levels. It has been established that the levels of muscular insulin-stimulated IR-beta, IRS-1 tyrosine phosphorylation, and IRS-1 associated with PI 3-kinase in HFD-fed rats are reduced −70+/−9%, −76+/−5%, and −72+/−6%, respectively, compared to controls (p<0.05), and the decreases were significantly improved by CE treatment. It is concluded that cinnamon extract reduces insulin resistance in the skeletal muscle (Quin B et al. Horm Metab Res. 2004; 36:119-125). T2DM subjects and subjects with normal glucose tolerance exhibited up to a 19% reduction in blood glucose (area under curve), after oral glucose tolerance tests (OGTT; 25 g of glucose), following administration of AG (3 g) (Vuksan et al. J Am Col Nutr. 2001, 20:370S-380S). Thus CE and AG have insulin sensitizing and blood glucose lowering effects.

As discovered within the present invention, serial administration of Comp1 (typically 4-8 weeks) and Comp2 (typically an additional 2-8 weeks) in mammals results surprisingly in a significant reduction of blood glucose levels. It was also known that components of Comp1 reduce biomarkers of obesity. Application of Comp1 to obese animals confirmed this (see Example 1). It was discovered that reduction of blood glucose levels is significantly greater following serial administration of Comp1 and Comp2 (Example 2), compared to Comp2 alone (Example 3). While not being bound by theory, Comp1 appears to sensitize physiological and pharmacological responses of subjects to the glucose lowering effect of Comp2.

Compositions 1 and 2

The typical amount of ingredients comprising Comp1 and Comp2 are given in Table 1. Preferred amounts of ingredients comprising Comp1 and Comp2 are given in Table 2. Magnesium salt may be selected from, but not limited to, magnesium chloride or magnesium citrate, fumarate, malate, glutarate, and succinate.

TABLE 1

Compositions of the Invention

| Composition | Ingredient | Amount (Daily) |
|---|---|---|
| 1 | (−)-HCA | 2 to 6 g |
| 1 | Mg | 1.5 to 4.5 |
| 1 | KM | 3.0 to 9.0 g |
| 2 | CrPic | 3.2 to 3.8 mg |
| 2 | α-LA | 1.2 to 1.8 g |
| 2 | Mg | 1.5 to 4.5 g |
| 2 | CE | 2 to 5 g |
| 2 | AG | 3 to 9 g |

(−)-HCA, (−)-Hydroxycitric acid;
Mg, magnesium chloride;
KM, konjac mannan (glucomannan);
CrPic, chromium picolinate;
α-LA, alpha-lipoic acid;
CE, cinnamon extract:
AG, American ginseng.
(−)-HCA is available as Super CitriMax from InterHealth Nutraceuticals, Benicia, CA.
Mg is available from Sigma Chemicals, St. Louis, MO (e.g., as $MgCl_2$).
KM is available from Fukar International Company Ltd., Taipai, Taiwan.
CrPic is available from Nutrition 21, NY, USA.
α-LA is available from Natrol Inc., CA, USA.
CE is available as Cinnulin PF from Integrity Nutraceuticals International, FL, USA.
AG is available from Superior Trading Company, CA, USA.

TABLE 2

Preferred Compositions of the Invention

| Composition | Ingredient | Amount (Daily) |
|---|---|---|
| 1 | (−)-HCA | 2.8 to 5 g |
| 1 | Mg | 2.5 g |
| 1 | KM | 3.6 g |
| 2 | CrPic | 3.2 mg |
| 2 | α-LA | 1.2 to 1.8 g |
| 2 | Mg | 2.5 g |
| 2 | CE | 2 to 5 g |
| 2 | AG | 3 g |

(−)-HCA, (−)-Hydroxycitric acid;
Mg, magnesium chloride;
KM, konjac mannan (glucomannan);
CrPic, chromium picolinate;
α-LA, alpha-lipoic acid;
CE, cinnamon extract:
AG, American ginseng Formulations of the Compositions The active components described for use herein can be included in a pharmaceutically suitable vehicle, selected to render such compositions amenable to delivery by oral, rectal, parenteral (e.g., intravenous, intramuscular, intra-arterial, intraperitoneal, and the like), or inhalation routes, osmotic pump, and the like. Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically and physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used.

The active compounds contemplated for use herein are included in the pharmaceutical composition in an amount sufficient to produce the desired effect upon the target process, condition or disease. In addition, such compositions may contain one or more agents selected from flavoring agents (such as peppermint, oil of wintergreen or cherry), coloring agents, preserving agents, and the like, in order to provide pharmaceutically elegant and palatable preparations.

Tablets containing the active ingredients in admixture with non-toxic pharmaceutically acceptable excipients may be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like.

Tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in U.S. Pat. Nos. 4,256,108; 4,160,452; and 4,265,874; to form osmotic therapeutic tablets for controlled release. When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for an example, peanut oil, liquid paraffin, olive oil and the like.

The pharmaceutical compositions may be in the form of a sterile injectable suspension. Such a suspension may be formulated according to known methods using suitable dispersing or wetting agents and suspending agents. The sterile injectable preparation may also be a sterile injectable solution or suspension in a non-toxic parenterally acceptable diluent or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like.

Buffers, preservatives, antioxidants, and the like can be incorporated as required. Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquefy and/or dissolve in the rectal cavity to release the active ingredients), and the like. In addition, sustained release systems, including semi-permeable polymer matrices in the form of shaped articles (e.g., films or microcapsules), may also be used for the administration of the active compounds employed herein.

The following Examples are offered by way of illustration and not by way of limitation.

EXAMPLES

Example 1

Fatty diabetic Zucker rats received the following for 4 weeks: (−)-HCA (400 mg/day), 2.5% KM in the diet and 3 g/L MgCl$_2$ in the drinking water. The following major changes were found compared to baseline: reduction of body weight by 5.8%, reduction of total cholesterol by up to 20%, and reduction of triglycerides by up to 35%. A statistically non-significant reduction in glucose level of −6.5% was observed.

Example 2

Fatty diabetic Zucker rats treated according to the procedure outlined in example 1 also received CrPic (20 mg/kg/day), α-LA (400 mg/kg/day) and 3 g/L MgCl$_2$ added to the drinking water for an additional 4 to 8 weeks. Glucose levels were reduced up to 35% compared to baseline.

Example 3

Fatty diabetic Zucker rats received CrPic (20 mg/kg/day), α-LA (400 mg/kg/day) and 3 g/L MgCl$_2$ added to the drinking water for 4 to 8 weeks. Glucose levels were reduced by up to 22% compared to baseline.

Example 4

Table 3 shows exemplary dosages and tablet amounts for certain components disclosed herein.

TABLE 3

Exemplary Dosages and Tablet Amounts

| Component | Dose per day | Dose Scheduling | Dose per tablet | Number of tablets per dose | Number of tablets per day |
|---|---|---|---|---|---|
| magnesium chloride | 2490 mg | once per day | 518 mg | 5 | 5 |
| konjac mannan | 3600 mg | 3 times per day at meals | 600 mg | 2 | 6 |
| alpha-lipoic acid | 1800 mg | 3 times per day | 300 mg | 2 | 6 |
| chromium picolinate | 400 μg chromium | once per day | 200 μg chromium | 2 | 2 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for treatment of diabetes and reduction of blood glucose level in a mammal in need thereof comprising administering to the mammal an effective amount of composition Comp1 for a period of from 4 to 8 weeks and subsequently administering to the mammal an effective amount of composition Comp2 for a period of from 2 to 8 weeks, said amounts of compositions Comp1 and Comp2 effective to treat diabetes and reduce blood glucose level, wherein composition Comp1 comprises (−)-hydroxycitric acid, konjac mannan and magnesium salt and wherein composition Comp2 comprises chromium picolinate, alpha-lipoic acid and magnesium salt.

2. The method of claim 1, wherein administering an effective amount of composition Comp1 comprises administering (−)-hydroxycitric acid (2 to 6 g/day), konjac mannan (3.0 to 9.0 g/day), and magnesium chloride (1.5 to 4.5 g/day).

3. The method of claim 1 wherein administering an effective amount of composition Comp2 comprises administering chromium picolinate (3.2 to 3.8 mg/day), alpha-lipoic acid (1.2 to 1.8 g/day), and magnesium chloride (1.5 to 4.5 g/day).

4. The method of claim 1 wherein administering an effective amount of composition Comp1 comprises administering (−)-hydroxycitric acid (2.8 to 5.6 g/day), magnesium chloride (2.5 g/day), and konjac mannan (3.6 g/day).

5. The method of claim 1 wherein administering an effective amount of composition Comp2 comprises administering chromium picolinate (3.2 mg/day), alpha-lipoic acid (1.2 to 1.8 g/day), and magnesium chloride (2.5 g/day).

6. The method of claim 1 wherein composition Comp1 and composition Comp2 further include a physiologically acceptable carrier which is suitable for oral, parenteral, enteral, rectal, sublingual or inhalation administration.

7. The method of claim 1 wherein said administering of compositions is oral, parenteral, enteral, rectal, sublingual, or via inhalation.

8. A method for treatment of hyperglycemia, oxidative stress, inflammation or side-effects associated with increases in glucose level in diabetes in a mammal in need thereof comprising administering to the mammal an effective amount of composition Comp1 for a period of from 4 to 8 weeks and subsequently administering to the mammal an effective amount of composition Comp2 for a period of from 2 to 8 weeks, said amounts effective to treat hyperglycemia, oxidative stress, inflammation or side-effects associated with increases in glucose level in diabetes, wherein composition Comp1 comprises (−)-hydroxycitric acid, konjac mannan and magnesium salt and wherein composition Comp2 comprises chromium picolinate, alpha-lipoic acid and magnesium salt.

9. The method of claim 8 wherein administering an effective amount of composition Comp 1 comprises administering (−)-hydroxycitric acid (2 to 6 g/day), konjac mannan (3.0 to 9.0 g/day), and magnesium chloride (1.5 to 4.5 g/day).

10. The method of claim 8 wherein administering an effective amount of composition Comp2 comprises administering chromium picolinate (3.2 to 3.8 mg/day), alpha-lipoic acid (1.2 to 1.8 g/day), and magnesium chloride (1.5 to 4.5 g/day).

11. The method of claim 8 wherein administering an effective amount of composition Comp1 comprises administering (−)-hydroxycitric acid (2.8 to 5.6 g/day), konjac mannan (3.6 g/day), and magnesium chloride (2.5 g/day).

12. The method of claim 8 wherein administering an effective amount of composition Comp2 comprises administering chromium picolinate (3.2 mg/day), alpha-lipoic acid (1.2 to 1.8 g/day), and magnesium chloride (2.5 g/day).

13. The method of claim 8 wherein composition Comp1 and composition Comp2 further include a physiologically acceptable carrier which is suitable for oral, parenteral, enteral, rectal, sublingual or inhalation administration.

14. The method of claim 8 wherein said administering of compositions is oral, parenteral, enteral, rectal, sublingual, or via inhalation.

15. The method of claim 2 wherein administering composition Comp1 and subsequently administering composition Comp2 results in a significant reduction of blood glucose level compared to administering composition Comp2 alone.

16. The method of claim 9 wherein administering composition Comp1 and subsequently administering composition Comp2 results in a significant reduction of blood glucose level compared to administering composition Comp2 alone.

* * * * *